US00PP09152P

United States Patent [19]

Enthoven

[11] Patent Number: Plant 9,152

[45] Date of Patent: May 30, 1995

[54] GERMANIUM PLANT NAMED MERIDONNA

[75] Inventor: Adrianus W. M. Enthoven, Wateringen, Netherlands

[73] Assignee: Enthoven Breeding B.V., Wateringen, Netherlands

[21] Appl. No.: 197,348

[22] Filed: Feb. 16, 1994

[51] Int. Cl.[6] ..... A01H 5/00

[52] U.S. Cl. ..... Plt./87.12

[58] Field of Search ..... Plt. 87.12

[56] References Cited

U.S. PATENT DOCUMENTS

P.P. 8,712 5/1994 Schumann ..... Plt./87.12

*Primary Examiner*—James R. Feyrer

*Attorney, Agent, or Firm*—Foley & Lardner

[57] ABSTRACT

A new and distinct cultivar of geranium named Meridonna, particularly characterized by the combined features of compact growth habit growing rather wide; foliage that is green with a light and very weak (RHS 137C) zone on the upperside; the left margins are double crenated and slightly wavy; the flower stalk is short, thick and grows above the plant; a large inflorescence with many open flowers; numerous flower buds that are elliptical in shape; semi-double flowers that are lilac-pink in color with a white-pink spot on the upper face of the lower flower petals; lower surface of the petals is 68D near the margin with a large white center; the plant branches spontaneously after a bud is present, flowering time is early and the plant flowers equally.

3 Drawing Sheets

The present invention comprises a new and distinct cultivar of geranium, botanically known as *Pelargonium zonale*, and hereinafter referred to by the cultivar name Meridonna.

Meridonna is product of a planned breeding program which has the objective of creating new geranium cultivars with double flower form, compact habit, fast rooting, good tolerance to Botrytis, superior weather resistance and little need for growth regulators.

Meridonna was originated from a hybridization made by the inventor in a controlled breeding program in Wateringen, The Netherlands in 1987. The female parent was an unnamed and proprietary Enthoven seedling, characterized by its compact growth. The male parent of Meridonna was an unnamed and proprietary Enthoven seedling, characterized by its weather resistance.

Meridonna was discovered and selected as one flowering plant within the progeny of the stated cross by Adrianus W. M. Endhoven in Jun. 1988 in a controlled environment in Wateringen, The Netherlands.

The first act of asexual reproduction of Meridonna was accomplished when vegetative cuttings were taken from the initial selection in Aug. 1988 in a controlled environment in Wateringen, The Netherlands under the supervision of Adrianus W. M. Enthoven.

Horticultural examination of selected units initiated in the spring and summer of 1989 and continuing thereafter has demonstrated that the combination of characteristics as herein disclosed for Meridonna are firmly fixed and are retained through successive generations of asexual reproduction.

Meridonna has not been observed under all possible environmental conditions. The phenotype may vary with variations in environment such as temperature, light intensity and day length, without, however, any variation in genotype.

The following measurements, and comparisons describe plants grown in Wateringen, The Netherlands under greenhouse and outdoor conditions which approximate those generally used in commercial practice.

The following traits have been repeatedly observed and are determined to be basic characteristics of Meridonna, which in combination distinguish this geranium as a new and distinct cultivar:

1. The plant has compact growth habit but grows rather wide.
2. The foliage is green with a light and very weak (RHS 137C) zone on the upper side.
3. The leaf margins are double crenated and slightly wavy.
4. The leaf stalk is green, short and sturdy.
5. The flower stalk is short, thick and grows above the plant.
6. The inflorescence is large with many open flowers.
7. The flower buds are numerous and elliptic in shape.
8. The flowers are semi-double and the color is lilac-pink with a white-pink spot on the upper face of the lower flower petals.
9. The flowering time is early to average and the plant flowers equally.
10. The plant branches spontaneously after a bud is present.
11. Due to the compact growth habit the plants do not need any growth regulators during the cultivation period.

Of the many commercial cultivars known to the present inventor, the most similar in comparison to Meridonna is the cultivar Blues disclosed in U.S. Plant Pat. No. 5,372. Reference is made to Chart A which compares certain characteristics of Meridonna to those same characteristics of Blues. In general comparison to Blues, Meridonna has, among other things, a clearly semi-double corolla, a different flower color as well as an elliptic bud shape.

The accompanying color photographic drawings show typical flower and foliage characteristics of Meridonna, with colors being as true as possible with illustrations of this type.

Sheet 1 is a side view of Meridonna grown in a 10.5 cm pot for approximately 8 weeks showing the foliage, flower stalks and inflorescences.

Sheet 2 is a close-up view of the upper and lower sides of typical leaf from Meridonna.

Sheet 3 is a close-up view of a typical flower from Meridonna showing the flower from the top and bottom.

In the following description color reference are made to The Royal Horticultural Society Colour Chart (R.H.S.) and Horticultural Colour Chart (H.C.C.). The color values were determined between 2:10 and 2:30 p.m. on Jul. 31, 1989 under 21,500 Klux light intensity at Wateringen, The Netherlands.

Classification:

*Botanical.*—A hybrid of the genus *Pelargonium zonale* cv. Meridonna.

*Commercial.*—Zontal geranium.

INFLORESCENCE

A. Umbel:

*Average diameter.*—Indoor: 114 mm.

*Average depth.*—Indoor: 94 mm.

*Peduncle length.*—Indoor: 147 mm.

*Pedical length.*—Indoor: 37 mm.

*Pedical color.*—Reddish green becoming dark red near top.

B. Corolla:

*Average diameter.*—Indoor: 48 cm.

*Form.*—Semi-double (7 to 9 petals).

*Color (general tonality at a distance of three meters)-.*—RHS 67D, HCC 625/1.

*Color (main body, upper surface).*—RHS 67D, HCC 719.

*Color dark spot center of upper face.*—RHS 57D.

*Color of veins on lower face.*—RHS 57D.

*Color (near margin upper face).*—RHS 67D - 68A, HCC 625/1 - HCC 625/1 - HCC 627/1.

*Color (general tonality lower side of petal).*—RHS 68D near margin with a large white center.

*Diameter lower petals.*—22 mm.

*Length lower petals.*—25 mm.

*Diameter upper petals.*—18 mm.

*Length upper petals.*—25 mm.

*Petal shape.*—Obovate.

*Sepal color.*—Green with dark-red veins.

C. Bud:

*Shape.*—Elliptic.

*Color.*—Lighter than corolla.

*Pedical.*—Red.

D. Reproduction organs:

*Androecium.*—7–9 anthers.

*Gynoecium.*—4–5 stigma.

E. Spring flowering:

*Response period.*—in Wateringen, The Netherlands in 1989, 62% of plants with at least 1 open flower 13 weeks after planting of unrooted cuttings.

F. Outdoor flower production: The flower count in 1989 in Wateringen, The Netherlands was between 41–46 flowers per plant from June through October observation period.

G. Durability: 100% shatter resistance.

PLANT

A. Foliage:

*Form.*—Kidney-shaped, with open base.

*Margin.*—Bicrenate.

*Color.*—Medium green (RHS 138A).

*Zonation.*—Light and very week (RHS 137C).

*Length.*—39 mm.

*Diameter.*—77 mm.

B. General appearance and form:

*Internode length.*—30 mm.

*Branching pattern.*—An average of 4.3 branches per plant.

*Height.*—231 mm.

C. Tolerance to Botrytis.—Good.

I claim:

1. A new and distinct cultivar of geranium plant named Meridonna, as illustrated and described.

* * * * *

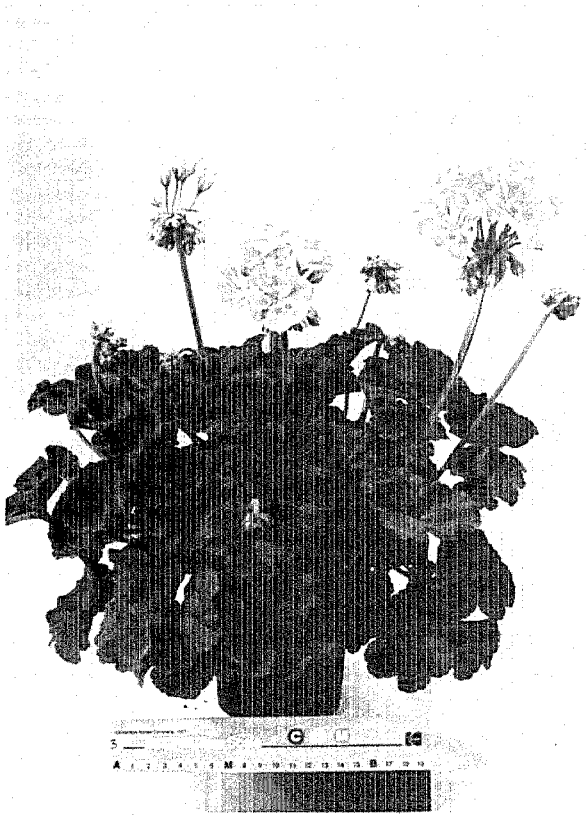

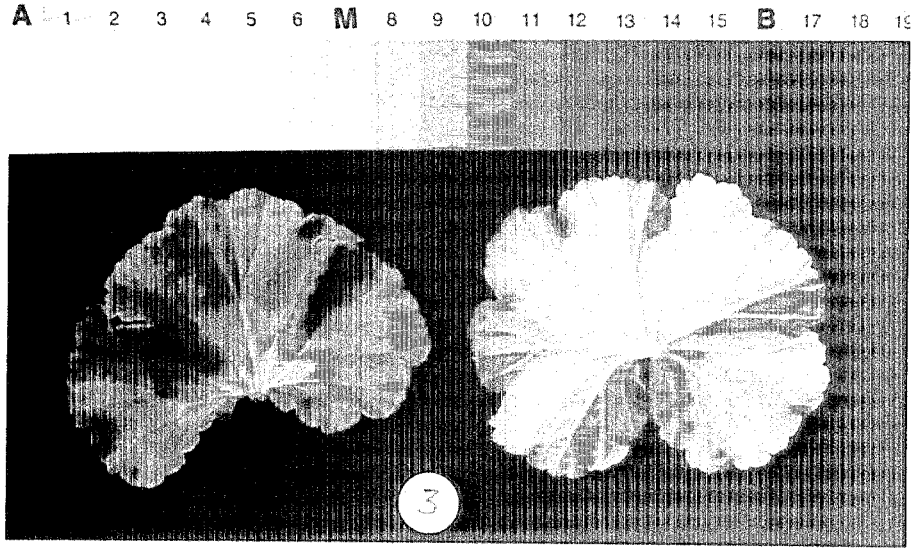
A 1 2 3 4 5 6 M 8 9 10 11 12 13 14 15 B 17 18 19
3

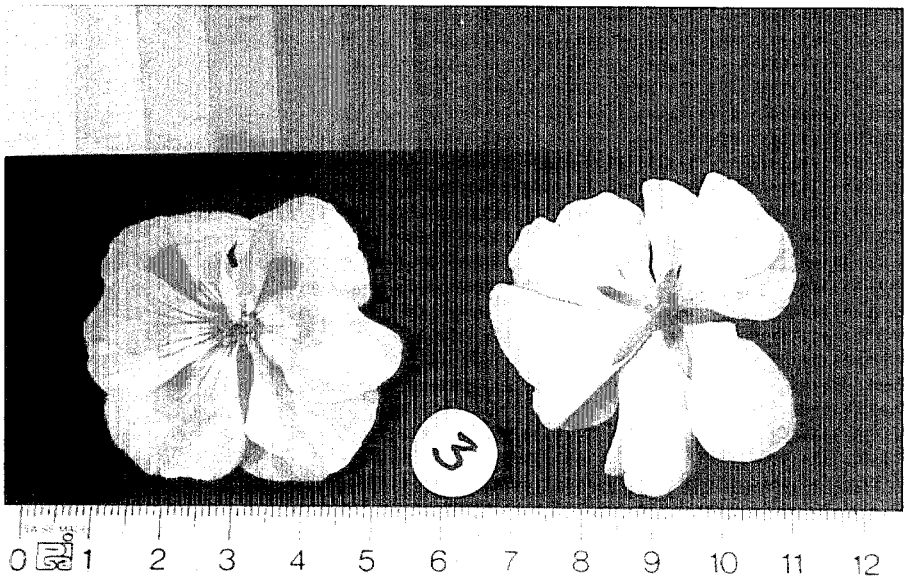
0
1
2
3
4
5
6
7
8
9
10
11
12